United States Patent
Inoue et al.

(10) Patent No.: US 12,269,806 B2
(45) Date of Patent: Apr. 8, 2025

(54) FLUX AND SOLDER PASTE

(71) Applicant: SENJU METAL INDUSTRY CO., LTD., Tokyo (JP)

(72) Inventors: Kenta Inoue, Tokyo (JP); Tomoko Takagi, Tokyo (JP)

(73) Assignee: SENJU METAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 18/692,201

(22) PCT Filed: Sep. 21, 2022

(86) PCT No.: PCT/JP2022/035051
§ 371 (c)(1),
(2) Date: Mar. 14, 2024

(87) PCT Pub. No.: WO2023/058450
PCT Pub. Date: Apr. 13, 2023

(65) Prior Publication Data
US 2024/0270706 A1    Aug. 15, 2024

(30) Foreign Application Priority Data
Oct. 6, 2021   (JP) ................................ 2021-164791

(51) Int. Cl.
*B23K 35/362* (2006.01)
*C07D 277/64* (2006.01)
*C22C 13/00* (2006.01)

(52) U.S. Cl.
CPC .......... *C07D 277/64* (2013.01); *B23K 35/362* (2013.01); *C22C 13/00* (2013.01)

(58) Field of Classification Search
CPC .................................................. B23K 35/362
See application file for complete search history.

(56) References Cited

FOREIGN PATENT DOCUMENTS

| | | |
|---|---|---|
| CN | 102666001 A | 9/2012 |
| CN | 104551451 A | 4/2015 |
| CN | 104923978 A | 9/2015 |
| CN | 107150190 A | 9/2017 |
| CN | 107717262 A | 2/2018 |
| EP | 1 952 935 A1 | 8/2008 |
| JP | 2002361484 A | 12/2002 |
| JP | 2004291019 A * | 10/2004 |
| WO | 2008105397 A1 | 9/2008 |

OTHER PUBLICATIONS

English machine translation of CN 104551451 A of Sun (Year: 2015).*
English machine translation of JP 2004-291019 A of Saito (Year: 2004).*
International Search Report for Application No. PCT/JP2022/035051, mailed Nov. 22, 2022 (4 pages).
Chinese Office Action for App. No. 202280066722.X, mailed Jun. 20, 2024 (7 pages) [English Search Report].
Notice of Allowance issued in Korean Application No. KR-10-2024-7011032, mailed Feb. 17, 2025 with Machine Translation (total 5 pages).

* cited by examiner

*Primary Examiner* — Jophy S. Koshy
(74) *Attorney, Agent, or Firm* — NIXON PEABODY LLP; Jeffrey L. Costellia (57) ABSTRACT

This flux contains a chelating agent and an organic acid. The chelating agent contains a compound (C) having a five-member ring structure comprising nitrogen atoms, sulfur atoms, and carbon atoms. The organic acid includes an organic sulfonic acid.

12 Claims, 1 Drawing Sheet

FLUX AND SOLDER PASTE

TECHNICAL FIELD

The present invention relates to a flux and a solder paste.
Priority is claimed on Japanese Patent Application No. 2021-164791, filed Oct. 6, 2021, the content of which is incorporated herein by reference.

BACKGROUND ART

Fixing of parts to substrates and electrical connection of parts to substrates are generally performed by soldering. A flux, a solder powder, and a solder paste in which the flux and the solder powder are mixed are used to conduct soldering.

A flux exhibits effects of chemically removing metal oxides present on the metal surface of an object to be soldered and a solder to allow metal elements to move at the boundary therebetween. Therefore, an intermetallic compound is formed therebetween and a strong bond can be obtained by performing soldering using the flux.

In soldering using a solder paste, the solder paste is first printed on a substrate, and then components are mounted thereon, followed by heating the substrate with the components mounted thereon in a heating furnace referred to as a reflow furnace. As a result, a solder powder contained in the solder paste is melted and the components are soldered to the substrate.

Ingredients in the flux are appropriately selected depending on the type of solder. For example, a solder paste using a flux containing a sulfur-containing organic compound containing divalent sulfur with a specific solder alloy powder is proposed in Patent Document 1.

CITATION LIST

Patent Document

Patent Document 1

Japanese Unexamined Patent Application Publication No. 2002-361484

SUMMARY OF INVENTION

Technical Problem

However, there is a case in which a solder in the solder paste described in Patent Document 1 exhibits low aggregability when melted at the time of reflow.

The aggregability of a solder is evaluated in accordance with the "4.2 Solder ball test" in JIS Z 3284-4:2014. In the case where the aggregability of a solder is low at the time of reflow, solder balls are easily generated. The solder balls may short electrical circuits on a substrate.

In addition, there is a case in which the viscosity of a solder paste increases over time by reacting an activator and a solder powder contained in the solder paste when stored before reflow.

Thus, the present invention aims to provide a flux and a solder paste that can suppress the viscosity increase of the solder paste over time and enhance the aggregability of a solder at the time of reflow.

Solution to Problem

The present invention adopts the following configuration so as to solve the above-mentioned problems.

Namely, the first aspect of the present invention is a flux containing: a chelate agent; and an organic acid, wherein the chelate agent contains a compound (C) having a five-membered ring structure consisting of nitrogen atoms, sulfur atoms and carbon atoms, and the organic acid contains an organic sulfonic acid.

In the flux of the first aspect, the compound (C) preferably contains at least one compound selected from the group consisting of compounds (C1) of the following general formula (1), compounds (C3) of the following general formula (3), and compounds (C7) of the following general formula (7).

[Chemical formula 1]

[In the formula, $R^{11}$ is an organic group, $-SR^{101}$, a hydrogen atom or a halogen atom. $R^{101}$ is an organic group or a hydrogen atom. $R^{12}$ is a substituent. n1 is an integer of 0 to 4. $R^{31a}$ and $R^{31b}$ are each independently an organic group, $-SR^{301}$, a hydrogen atom or a halogen atom. $R^{301}$ is an organic group or a hydrogen atom. $R^{41}$ is an organic group, $-SR^{401}$, a hydrogen atom or a halogen atom. $R^{401}$ is an organic group or a hydrogen atom. $R^{42a}$ and $R^{42b}$ are each independently an organic group, $-SR^{402}$, a hydrogen atom or a halogen atom. $R^{402}$ is an organic group or a hydrogen atom. $R^{43a}$ and $R^{43b}$ are each independently an organic group, $-SR^{403}$, a hydrogen atom or a halogen atom. $R^{403}$ is an organic group or a hydrogen atom.]

In the flux of the first aspect, the amount of the compound (C) relative to the total mass (100% by mass) of the flux is 0.1% by mass to 3% by mass.

In the flux of the first aspect, the ratio (mass ratio) of the amount of the organic sulfonic acid relative to the total mass of the compound (C) is 0.3 to 10

In the flux of the first aspect, it is preferable that a rosin be further contained.

In the flux of the first aspect, it is preferable that a thixotropic agent be further contained.

The second aspect of the present invention is a solder paste containing a solder alloy powder and the flux of the first aspect.

Advantageous Effects of Invention

The present invention makes it possible to provide a flux and a solder paste which can suppress the viscosity increase of a solder paste over time and can enhance the aggregability of a solder at the time of reflow.

DESCRIPTION OF EMBODIMENTS (Flux)

A flux according to the present embodiment contains a chelate agent and an organic sulfonic acid.

In the present invention, the term "chelate agent" refers to a compound which can form a chelate complex with a metal on the surface of a solder powder in a solder paste to protect the surface of the solder powder.

<Chelate Agent>

A chelate agent contained in the flux of the present embodiment contains a compound (C) having a five-membered ring structure consisting of nitrogen atoms, sulfur atoms and carbon atoms.

<<Compound (C)>>

The chelate agent contained in the flux of the present embodiment may consist of a compound (C), or may contain a compound (C) and another chelate agent different from the compound (C).

The five-membered ring structure in the compound (C) is a hetero ring. The five-membered ring structure may contain one or two nitrogen atom(s), and one sulfur atom. The five-membered ring structure may have one or two 7c bond(s). The five-membered ring structure may be an alicyclic hydrocarbon group or an aromatic ring. The compound (C) may form a condensed ring with the five-membered ring structure and an aromatic ring.

Examples of the compound (C) include compounds (C1) of the following general formula (1), compounds (C2) of the following general formula (2), compounds (C3) of the following general formula (3), compounds (C4) of the following general formula (4), compounds (C5) of the following general formula (5), compounds (C6) of the following general formula (6), compounds (C7) of the following general formula (7), compounds (C8) of the following general formula (8), and compounds (C9) of the following general formula (9).

[Compound (C1)]

The compound (C1) is a compound of the following general formula (1).

[Chemical formula 2]

(1)

[In the formula, $R^{11}$ is an organic group, $-SR^{101}$, a hydrogen atom or a halogen atom. $R^{101}$ is an organic group or a hydrogen atom. $R^{12}$ is a substituent. n1 is an integer of 0 to 4.]

In the case where $R^{11}$ is an organic group, $R^{11}$ is, for example, a C1-20 chained hydrocarbon group which may have a substituent, a C3-20 alicyclic hydrocarbon group which may have a substituent, an amino group, a hydroxy group, a carboxy group, or the like.

In the case where $R^{11}$ is a chained hydrocarbon group, the chained hydrocarbon group may be linear or branched. The chained hydrocarbon group is a saturated hydrocarbon group or an unsaturated hydrocarbon group, and is preferably a saturated hydrocarbon group.

In the case where $R^{11}$ is an alicyclic hydrocarbon group, the alicyclic hydrocarbon group may be a polycyclic group or a monocyclic group. The monocyclic alicyclic hydrocarbon group is preferably a group formed by removing at least one hydrogen atom from a monocycloalkane. The polycyclic alicyclic hydrocarbon group is preferably a group formed by removing at least one hydrogen atom from a polycycloalkane.

Examples of the substituent in $R^{11}$ include an amino group, a hydroxy group, a carboxy group, acyl groups, alkoxy groups, carbonyl groups, and halogen atoms.

In the case where $R^{11}$ is $-SR^{101}$, $R^{101}$ is an organic group or a hydrogen atom. In the case where $R^{101}$ is an organic group, a C1-20 chained hydrocarbon group which may have a substituent, a C3-20 alicyclic hydrocarbon group which may have a substituent, or the like can be mentioned as the organic group. The description of the chained hydrocarbon group and the alicyclic hydrocarbon group as $R^{101}$ is the same as the description of the chained hydrocarbon group and the alicyclic hydrocarbon group as $R^{11}$ mentioned above. Examples of the substituent in $R^{101}$ include the same groups as those mentioned as the substituent in $R^{11}$ above.

$R^{101}$ is preferably a chained hydrocarbon group or a hydrogen atom, more preferably a C1-10 chained hydrocarbon group or a hydrogen atom, and even more preferably a C1-5 chained hydrocarbon group or a hydrogen atom, and particularly preferably a hydrogen atom.

Examples of the hydrocarbon group as $R^{101}$ include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, and a neopentyl group.

Examples of the halogen atom as $R^{11}$ include a fluorine atom, a chlorine atom, a bromine atom, and an iodine atom.

$R^{11}$ is preferably $-SR^{101}$.

$R^{12}$ is, for example, a C1-5 hydrocarbon group, a carboxy group, a hydroxy group, an amino group, or a halogen atom. The hydrocarbon group as $R^{12}$ may have a substituent.

Examples of the substituent in the hydrocarbon group include the same groups as those mentioned as a substituent in $R^{11}$ above.

In the case where n1 is two or more, plural $R^{12}$ may be identical to or different from each other. n1 is preferably 0.

Examples of the compound (C1) include 2-mercaptobenzothiazole, 2-(methylthio)benzothiazole, 2-chlorobenzothiazole, 2-methylbenzothiazole, 5-methoxy-2-methylbenzothiazole, 2-aminobenzothiazole, 2-amino-6-methylbenzothiazole, 2-amino-4-methoxybenzothiazole, and 4-methyl-2-mercaptobenzothiazole.

Among these, the compound (C1) is preferably 2-mercaptobenzothiazole. The 2-mercaptobenzothiazole is a compound of the following formula (C1-1).

[Chemical formula 3]

(C1-1)

[Compound (C2)]

The compound (C2) is a compound of the following general formula (2). In the five-membered ring of the compound (C2), a nitrogen atom and a sulfur atom are adjacent to each other.

[Chemical formula 4]

(2)

[In the formula, $R^{21}$ is an organic group, $-SR^{201}$, a hydrogen atom or a halogen atom. $R^{22}$ is a substituent. n2 is an integer of 0 to 4.]

As $R^{21}$, the same groups as those mentioned as $R^{11}$ in the above-mentioned general formula (1) can be mentioned.

As $-SR^{201}$, the same groups as those mentioned as $-SR^{101}$ can be mentioned.

As the halogen atom as $R^{21}$, the same atoms as those mentioned as $R^{11}$ can be mentioned.

As $R^{22}$, the same groups as those mentioned as $R^{12}$ in the above-mentioned general formula (1) can be mentioned.

In the case where n2 is 2 or more, plural $R^{22}$ may be identical to or different from each other. n2 is preferably 0.

Examples of the compound (C2) include 1,2-benzoisothiazole, 3-chloro-1,2-benzisothiazole, and 1-(1,2-benzisothiazol-3-yl)piperazine.

Compound (C3)

The compound (C3) is a compound of the following general formula (3). The compound (C3) is referred to as a 1,3,4-thiadiazole derivative.

[Chemical formula 5]

(3)

[In the formula, $R^{31a}$ and $R^{31b}$ are each independently an organic group, $-SR^{101}$, a hydrogen atom or a halogen atom. $R^{301}$ is an organic group or a hydrogen atom.]

As $R^{31a}$ and $R^{31b}$, the same groups as those mentioned as $R^{11}$ in the above-mentioned general formula (1) can be mentioned.

As $-SR^{301}$, the same groups as those mentioned as $-SR^{101}$ can be mentioned.

As the halogen atom as $R^{31a}$ and $R^{31b}$, the same groups as those mentioned as $R^{11}$ can be mentioned.

$R^{31a}$ and $R^{31b}$ are each independently and preferably $-SR^{301}$, and more preferably $-SH$.

Examples of the compound (C3) include 2,5-dimercapto-1,3,4-thiadiazole, 2-methyl-1,3,4-thiadiazole-5-thiol, 2-mercapto-1,3,4-thiadiazole, 2,5-dimethyl-1,3,4-thiadiazole, and 2,5-diethyl-1,3,4-thiadiazole.

Among these, the compound (C3) is preferably 2,5-dimercapto-1,3,4-thiadiazole. The 2,5-dimercapto-1,3,4-thiadiazole is a compound of the following formula (C3-1).

[Chemical formula 6]

(C3-1)

Compound (C4)

The compound (C4) is a compound of the following general formula (4). The compound (C4) is a 1,2,3-thiadiazole derivative.

[Chemical formula 7]

(4)

[In the formula, $R^{32}$ is an organic group, $-SR^{302}$, a hydrogen atom or a halogen atom. $R^{302}$ is an organic group or a hydrogen atom. $R^{33}$ is an organic group, $-SR^{303}$, a hydrogen atom or a halogen atom. $R^{303}$ is an organic group or a hydrogen atom.]

In the compound (C4) of the general formula (4), the same groups as those mentioned as $R^{11}$ in the general formula (1) can be mentioned as $R^{32}$. The same groups as those mentioned as $R^{11}$ in the general formula (1) can be mentioned as $R^{33}$.

As $-SR^{302}$, the same groups as those mentioned as $-SR^{101}$ can be mentioned. As $-SR^{303}$, the same groups as those mentioned as $-SR^{101}$ can be mentioned.

As the halogen atom as $R^{32}$, the same atoms as those mentioned as $R^{11}$ can be mentioned. As the halogen atom as $R^{33}$, the same atoms as those mentioned as $R^{11}$ can be mentioned.

Examples of the compound (C4) include 1,2,3-thiadiazole, and 4,5-dimercapto-1,2,3-thiadiazole.

Compound (C5)

The compound (C5) is a compound of the following general formula (5). The compound (C5) is a 1,2,5-thiadiazole derivative.

[Chemical formula 8]

(5)

[In the formula, $R^{34a}$ and R are each independently an organic group, $-SR^{304}$, a hydrogen atom or a halogen atom. $R^{304}$ is an organic group or a hydrogen atom.]

In the compound (C5) of the general formula (5), $R^{34a}$ and $R^{34b}$ are each independently the same groups as those mentioned as $R^{11}$ in the general formula (1).

As $-SR^{304}$, the same groups as those mentioned as $-SR^{101}$ can be mentioned.

As the halogen atom as $R^{34a}$ and $R^{34b}$, the same atoms as those mentioned as $R^1$ can be mentioned.

Examples of the compound (C5) include 1,2,5-thiadiazole, and 3,4-dimercapto-1,2,5-thiadiazole.

Compound (C6)

The compound (C6) is a compound of the following general formula (6). The compound (C6) is a 1,2,4-thiadiazole derivative.

[Chemical formula 9]

(6)

[In the formula, $R^{35}$ is an organic group, $-SR^{305}$, a hydrogen atom or a halogen atom. $R^{305}$ is an organic group or a hydrogen atom. $R^{36}$ is an organic group, $-SR^{306}$, a hydrogen atom or a halogen atom. $R^{306}$ is an organic group or a hydrogen atom.]

In the compound (C6) of the general formula (6), the same groups as those mentioned as $R^{11}$ in the general formula (1) can be mentioned as $R^{35}$. The same groups as those mentioned as $R^{11}$ in the general formula (1) can be mentioned as $R^{36}$.

The same groups as those mentioned as $-SR^{101}$ can be mentioned as $-SR^{305}$. The same groups as those mentioned as $-SR^{101}$ can be mentioned as $-SR^{306}$.

As the halogen atom as $R^{35}$, the same atoms as those mentioned as $R^{11}$ can be mentioned. As the halogen atom as $R^{36}$, the same atoms as those mentioned as $R^{11}$ can be mentioned.

Examples of the compound (C6) include 1,2,4-thiadiazole, and 3,5-dimercapto-1,2,4-thiadiazole.

Compound (C7)

The compound (C7) is a compound of the following general formula (7).

[Chemical formula 10]

(7)

[In the formula, $R^{41}$ is an organic group, $-SR^{401}$, a hydrogen atom or a halogen atom. $R^{401}$ is an organic group or a hydrogen atom. $R^{42a}$ and $R^{42b}$ are each independently an organic group, $-SR^{402}$, a hydrogen atom or a halogen atom. $R^{402}$ is an organic group or a hydrogen atom. $R^{43a}$ and $R^{43b}$ are each independently an organic group, $-SR^{403}$, a hydrogen atom or a halogen atom. $R^{403}$ is an organic group or a hydrogen atom.]

The same groups as those mentioned as $R^{11}$ in the general formula (1) can be mentioned as $R^{41}$.

The same groups as those mentioned as $R^{101}$ in the general formula (1) can be mentioned as $R^{401}$. $R^{401}$ is preferably a C1-5 chained hydrocarbon group, and more preferably a methyl group.

As the halogen atom as $R^{41}$, the same atoms as those mentioned as $R^{11}$ can be mentioned.

$R^{41}$ is preferably $-SR^{401}$.

As $R^{42a}$ and $R^{42b}$, the same groups as those mentioned as $R^{11}$ in the general formula (1) can be each mentioned independently. As $-SR^{402}$, the same groups as those mentioned as $-SR^{101}$ can be mentioned. It is preferable that $R^{42a}$ and $R^{42b}$ be each independently a C1-5 chained hydrocarbon group or a hydrogen atom, and more preferably a hydrogen atom.

As the halogen atom as $R^{42a}$ and $R^{42b}$, the same atoms as those mentioned as $R^1$ can be mentioned.

As $R^{43a}$ and $R^{43b}$, the same groups as those mentioned as $R^{11}$ in the general formula (1) can be each mentioned independently. As $-SR^{403}$, the same groups as those mentioned as $-SR^{101}$ can be mentioned. $R^{43a}$ and $R^{43b}$ are each independently and preferably a C1-5 chained hydrocarbon group or a hydrogen atom, and more preferably a hydrogen atom.

As the halogen atom as $R^{43a}$ and $R^{43b}$, the same atoms as those mentioned as $R^1$ can be mentioned.

Examples of the compound (C7) include 2-(methylthio)-2-thiazoline, 2-mercaptothiazoline, 2-methylthiazoline, 2-methyl-4-ethylthiazoline, and 2-acetyl-2-thiazoline.

Among these, the compound (C7) is preferably 2-(methylthio)-2-thiazoline. The 2-(methylthio)-2-thiazoline is a compound of the following formula (C7-1).

[Chemical formula 11]

(C7-1)

Compound (C8)

The compound (C8) is a compound of the following general formula (8)

[Chemical formula 12]

(8)

[In the formula, $R^{51a}$ and $R^{51b}$ are each independently an organic group, $-SR^{101}$, a hydrogen atom or a halogen atom. $R^{501}$ is an organic group or a hydrogen atom. $R^{52a}$ and $R^{52b}$ are each independently an organic group, $-SR^{502}$, a hydrogen atom or a halogen atom. $R^{502}$ is an organic group or a hydrogen atom. $R^{53}$ is an organic group, $-SR^{503}$, a hydrogen atom or a halogen atom. $R^{503}$ is an organic group or a hydrogen atom.]

As $R^{51a}$ and $R^{51b}$, the same groups as those mentioned as $R^{11}$ in the general formula (1) can be each mentioned independently. As $-SR^{501}$, the same groups as those mentioned as $-SR^{101}$ can be mentioned.

As the halogen atom as $R^{51a}$ and $R^{51b}$, the same atoms as those mentioned as $R^{11}$ can be mentioned.

As $R^{52a}$ and $R^{52b}$, the same groups as those mentioned as $R^{11}$ in the general formula (1) can be each mentioned independently. As $-SR^{202}$, the same groups as those mentioned as $-SR^{101}$ can be mentioned.

As the halogen atom as $R^{52a}$ and $R^{52b}$, the same atoms as those mentioned as $R^{11}$ can be mentioned.

As $R^{53}$, the same groups as those mentioned as $R^{11}$ in the general formula (1) can be mentioned.

As the halogen atom as $R^{53}$, the same atoms as those mentioned as $R^{11}$ can be mentioned.

Examples of the compound (C8) include 2-isobutyl-4,5-dimethyl-3-thiazoline.

Compound (C9)

The compound (C9) is a compound of the following general formula (9).

[Chemical formula 13]

(9)

[In the formula, $R^{61a}$ and $R^{61b}$ are each independently an organic group, $-SR^{601}$, a hydrogen atom or a halogen atom. $R^{601}$ is an organic group or a hydrogen atom. $R^{62}$ is an organic group, $-SR^{602}$, a hydrogen atom or a halogen atom. $R^{602}$ is an organic group or a hydrogen atom. $R^{63}$ is an organic group, $-SR^{603}$, a hydrogen atom or a halogen atom. $R^{603}$ is an organic group or a hydrogen atom. $R^{64}$ is an organic group, $-SR^{604}$, a hydrogen atom or a halogen atom. $R^{604}$ is an organic group or a hydrogen atom.]

As $R^{61a}$ and $R^{61b}$, the same groups as those mentioned as $R^{11}$ in the general formula (1) can be each mentioned independently. As $-SR^{601}$, the same groups as those mentioned as $-SR^{101}$ can be mentioned.

As the halogen atom as $R^{61a}$ and $R^{61b}$, the same atoms as those mentioned as $R^{11}$ can be mentioned.

As $R^{62}$, the same groups as those mentioned as $R^{11}$ in the general formula (1) can be mentioned. As $-SR^{602}$, the same groups as those mentioned as $-SR^{101}$ can be mentioned.

As the halogen atom as $R^{62}$, the same atoms as those mentioned as $R^{11}$ can be mentioned.

As $R^{63}$, the same groups as those mentioned as $R^{11}$ in the general formula (1) can be mentioned. As $-SR^{603}$, the same groups as those mentioned as $-SR^{101}$ can be mentioned.

As the halogen atom as $R^{63}$, the same atoms as those mentioned as $R^{11}$ can be mentioned.

As $-SR^{604}$, the same groups as those mentioned as $-SR^{101}$ can be mentioned.

As the halogen atom as $R^{64}$, the same atoms as those mentioned as $R^{11}$ can be mentioned.

One of the compounds (C) may be used alone or at least two thereof may be mixed and used.

The compound (C) preferably contains at least one compound selected from the group consisting of the compounds (C1), the compounds (C2), the compounds (C3), the compounds (C4), the compounds (C5), the compounds (C6), the compounds (C7), the compounds (C8), and the compounds (C9).

The compound (C) more preferably contains at least one compound selected from the group consisting of the compounds (C1), the compounds (C3), and the compounds (C7).

In the flux, the amount of the compound (C) relative to the total mass (100% by mass) of the flux is 0.1% by mass to 3% by mass, and more preferably 0.5% by mass to 3% by mass.

The viscosity increase of a solder paste over time can be further easily suppressed by making the amount of the compound (C) be the above-mentioned lower limit or more.

The wettability can be further easily maintained by making the amount of the compound (C) be the above-mentioned upper limit or less.

Other Chelate Agent

The flux according to the present embodiment may contain other chelate agents different from the compound (C). Examples of other chelate agents include 2-mercaptopyridine, sodium ethylenediaminetetraacetate, sodium diethyldithiocarbamate, thiourea, phenanthroline, and 2,3-dimercaptopropanol.

In the flux, the total amount of the chelate agent relative to the total mass of the flux (100% by mass) is preferably 0.1% by mass to 5% by mass, and more preferably 0.1% by mass to 3% by mass.

In the flux, the amount of the compound (C) relative to the total mass (100% by mass) of the chelate agent may be 50% by mass or more, 60% by mass or more, 70% by mass or more, 80% by mass or more, 90% by mass or more, or 100% by mass.

The viscosity increase of a solder paste over time can be further easily suppressed by making the amount of the compound (C) be the above-mentioned lower limit or more. The wettability can be further easily maintained by making the amount of the compound (C) be the above-mentioned upper limit or less.

<Organic acid>

An organic acid contained in the flux according to the present embodiment contains an organic sulfonic acid.

<<Organic sulfonic acid>>

Examples of the organic sulfonic acid include aliphatic sulfonic acids and aromatic sulfonic acids. Examples of the aliphatic sulfonic acid include alkanesulfonic acids and alkanolsulfonic acids.

Examples of the alkanesulfonic acids include methanesulfonic acid, ethanesulfonic acid, 1-propanesulfonic acid, 2-propanesulfonic acid, 1-butanesulfonic acid, 2-butanesulfonic acid, pentanesulfonic acid, hexanesulfonic acid, decanesulfonic acid, and dodecanesulfonic acid.

Examples of the alkanolsulfonic acids include 2-hydroxyethane-1-sulfonic acid, 2-hydroxypropane-1-sulfonic acid, 2-hydroxybutane-1-sulfonic acid, 2-hydroxypentane-1-sulfonic acid, 1-hydroxypropane-2-sulfonic acid, 3-hydroxypropane-1-sulfonic acid, 4-hydroxybutane-1-sulfonic acid, 2-hydroxyhexane-1-sulfonic acid, 2-hydroxydecane-1-sulfonic acid and 2-hydroxydodecane-1-sulfonic acid.

Examples of the aromatic sulfonic acids include 1-naphthalenesulfonic acid, 2-naphthalenesulfonic acid, p-toluenesulfonic acid, xylenesulfonic acid, p-phenolsulfonic acid, cresolsulfonic acid, sulfosalicylic acid, nitrobenzenesulfonic acid, sulfobenzoic acid and diphenylamine-4-sulfonic acid.

One of the organic sulfonic acids may be used alone or at least two thereof may be mixed and used.

The organic sulfonic acid preferably contains at least one selected from the group consisting of aliphatic sulfonic acids and aromatic sulfonic acids.

The organic sulfonic acid more preferably contains an aromatic sulfonic acid, and even more preferably contains p-toluenesulfonic acid.

Alternatively, the organic sulfonic acid preferably contains an aliphatic sulfonic acid, and the aliphatic sulfonic acid preferably contains an alkanesulfonic acid, and more preferably contains a methanesulfonic acid.

In the flux, the amount of the organic sulfonic acid relative to the total mass (100% by mass) of the flux is preferably 0.5% by mass to 1.5% by mass, and more preferably 1.0% by mass to 1.5% by mass.

The aggregability of a solder at the time of reflow tends to be further enhanced by making the amount of the organic sulfonic acid be the above-mentioned lower limit or more. The viscosity increase of a solder paste overtime tends to be suppressed by making the amount of the organic sulfonic acid be the above-mentioned upper limit or less.

The mixing ratio of the organic sulfonic acid and the compound (C), indicated by the mass ratio of the organic sulfonic acid/the compound (C), namely, the ratio of the total mass of the organic sulfonic acid relative to the total mass of the compound (C), is preferably 0.3 to 10. The viscosity increase of a solder paste over time is easily suppressed and the aggregability of a solder at the time of reflow is easily enhanced by making the mixing ratio be within the above-mentioned range.

The flux according to the present embodiment may contain other organic acids different from the organic sulfonic acid.

<<Other Organic Acids>>

Examples of other organic acids include carboxylic acids.

Examples of the carboxylic acids include aliphatic carboxylic acids and aromatic carboxylic acids.

Examples of an organic acid-based activator include oxalic acid, malonic acid, succinic acid, glutaric acid, adipic acid, azelaic acid, eicosanedioic acid, salicylic acid, dipicolinic acid, dibutyl aniline diglycolic acid, suberic acid, sebacic acid, terephthalic acid, dodecanedioic acid, parahydroxyphenylacetic acid, picolinic acid, phenylsuccinic acid, phthalic acid, lauric acid, benzoic acid, tartaric acid, tris(2-carboxyethyl) isocyanurate, 1,3-cyclohexanedicarboxylic acid, 2,2-bis(hydroxymethyl)propionic acid, 2,2-bis(hydroxymethyl)butanoic acid, 2,3-dihydroxybenzoic acid, 2,4-diethylglutaric acid, 2-quinolinecarboxylic acid, 3-hydroxybenzoic acid, p-anisic acid, stearic acid, 12-hydroxystearic acid, oleic acid, linoleic acid, linolenic acid, myristic acid, palmitic acid, pimelic acid, caproic acid, enanthic acid, caprylic acid, pelargonic acid, isopelargonic acid, capric acid, caproleic acid, undecanoic acid, linderic acid, tridecanoic acid, myristoleic acid, pentadecanoic acid, isopalmitic acid, palmitoleic acid, hiragonic acid, hydnocarpic acid, margaric acid, isostearic acid, elaidic acid, petroselinic acid, moroctic acid, eleostearic acid, tariric acid, vaccenic acid, ricinoleic acid, vernolic acid, sterculynic acid, nonadecanoic acid, eicosanoic acid, dimer acid, trimer acid, hydrogenated dimer acid which is a hydrogenated product formed by adding hydrogen to dimer acid, and hydrogenated trimer acid which is a hydrogenated product formed by adding hydrogen to trimer acid.

Examples of the dimer acid and the trimer acid include dimer acid which is a reaction product of oleic acid and linoleic acid, trimer acid which is a reaction product of oleic acid and linoleic acid, dimer acid which is a reaction product of acrylic acid, trimer acid which is a reaction product of acrylic acid, dimer acid which is a reaction product of methacrylic acid, trimer acid which is a reaction product of methacrylic acid, dimer acid which is a reaction product of acrylic acid and methacrylic acid, trimer acid which is a reaction product of acrylic acid and methacrylic acid, dimer acid which is a reaction product of oleic acid, trimer acid which is a reaction product of oleic acid, dimer acid which is a reaction product of linoleic acid, trimer acid which is a reaction product of linoleic acid, dimer acid which is a reaction product of linolenic acid, trimer acid which is a reaction product of linolenic acid, dimer acid which is a reaction product of acrylic acid and oleic acid, trimer acid which is a reaction product of acrylic acid and oleic acid, dimer acid which is a reaction product of acrylic acid and linoleic acid, trimer acid which is a reaction product of acrylic acid and linoleic acid, dimer acid which is a reaction product of acrylic acid and linolenic acid, trimer acid which is a reaction product of acrylic acid and linolenic acid, dimer acid which is a reaction product of methacrylic acid and oleic acid, trimer acid which is a reaction product of methacrylic acid and oleic acid, dimer acid which is a reaction product of methacrylic acid and linoleic acid, trimer acid which is a reaction product of methacrylic acid and linoleic acid, dimer acid which is a reaction product of methacrylic acid and linolenic acid, trimer acid which is a reaction product of methacrylic acid and linolenic acid, dimer acid which is a reaction product of oleic acid and linolenic acid, trimer acid which is a reaction product of oleic acid and linolenic acid, dimer acid which is a reaction product of linoleic acid and linolenic acid, trimer acid which is a reaction product of linoleic acid and linolenic acid, hydrogenated dimer acid which is a hydrogenated product of each of the above-mentioned dimer acids, and hydrogenated trimer acid which is a hydrogenated product of each of the above-mentioned trimer acid.

For example, a dimer acid which is a reaction product of oleic acid and linoleic acid is a dimer having 36 carbon atoms. Furthermore, a trimer acid which is a reaction product of oleic acid and linoleic acid is a trimer having 54 carbon atoms.

One of other organic acids may be used alone or at least two thereof may be mixed and used.

Other organic acids preferably contain a carboxylic acid, more preferably contain an aliphatic carboxylic acid, even more preferably contain an aliphatic dicarboxylic acid, and particularly preferably contain at least one selected from the group consisting of glutaric acid, adipic acid and azelaic acid.

In the flux, the amount of other organic acids relative to the total mass (100% by mass) of the flux is preferably 3% by mass to 20% by mass, and more preferably 5% by mass to 15% by mass.

In the flux, the total amount of the organic acid relative to the total mass (100% by mass) of the flux is preferably 5% by mass to 25% by mass, more preferably 8% by mass to 20% by mass, and even more preferably 10% by mass to 15% by mass.

In the flux, the amount of the organic sulfonic acid relative to the total mass (100% by mass) of the organic acid is preferably 1% by mass or more, more preferably 3% by mass to 30% by mass, even more preferably 5% by mass to 30% by mass, even more preferably 5% by mass to 20% by mass, particularly preferably 5% by mass to 15% by mass and most preferably 5% by mass to 10% by mass.

The suppressibility of solder ball formation tends to be easily improved by making the amount of the organic sulfonic acid be the above-mentioned lower limit or more. The viscosity increase of a solder paste over time tends to be easily suppressed and the possibility of generating precipitate which causes clumping tends to be easily suppressed by making the amount of the organic sulfonic acid be the above-mentioned upper limit or less.

<Other Components>

The flux according to the present embodiment may contain other components in addition to the chelate agent and the organic acid, as needed.

Examples of other components include: activators other than rosins, thixotropic agents, solvents, or organic acid (other activator); resin components other than rosins; metal deactivators; surfactants; silane coupling agents; antioxidants; and colorants.

<<Rosin>>

In the present invention, the term "rosin" encompasses: natural resins including a mixture of an abietic acid as the main component and isomers thereof; and ones obtained by chemically modifying natural resins (which may be referred to as rosin derivatives).

The amount of the abietic acid in the natural resin relative to the natural resin is 40% by mass to 80% by mass, for example.

In the present specification, the term "main component" refers to a component the amount of which in a compound relative to the total mass of components constituting the compound is 40% by mass or more.

Representative examples of the isomer of the abietic acid include neoabietic acid, palustric acid, and levopimaric acid. The structure of the abietic acid is shown below.

[Chemical formula 14]

Abietic acid

Examples of the "natural resin" include gum rosin, wood rosin and tall oil rosin.

In the present invention, the term "ones obtained by chemically modifying natural resins (rosin derivatives)" encompasses ones obtained by subjecting the above-mentioned "natural resin" to one or more treatments selected from the group consisting of hydrogenation, dehydrogenation, neutralization, alkylene oxide addition, amidation, dimerization, multimerization, esterification, and Diels-Alder cycloaddition.

Examples of the rosin derivatives include purified rosins and modified rosins.

Examples of the modified rosins include: hydrogenated rosins; polymerized rosins; polymerized hydrogenated rosins; heterogeneous rosins; acid-modified rosins; rosin esters; acid-modified hydrogenated rosins; anhydrous acid-modified hydrogenated rosins; acid-modified heterogeneous rosins; anhydrous acid-modified heterogeneous rosins; phenol-modified rosins; α,β unsaturated carboxylic acid-modified products (such as acrylated rosins, maleated rosins, and fumarated rosins); purified products, hydrogenated products and heterogeneous products of the polymerized rosin; purified products, hydrogenated products and heterogeneous products of the α,β unsaturated carboxylic acid-modified products; rosin alcohols; rosin amines; hydrogenated rosin alcohols; rosin esters; hydrogenated rosin esters; rosin soaps; hydrogenated rosin soaps; and acid-modified rosin soaps.

Examples of the rosin amine include dehydroabietylamine, and dihydroabietylamine. The term "rosin amine" means a so-called heterogeneous rosin amine. Each structure of dehydroabietylamine and dihydroabietylamine is shown below.

[Chemical formula 15]

Dehydrobietylamine    Dehydrobietylamine

One of the rosins may be used alone or at least two thereof may be mixed and used.

The rosin preferably contains a rosin derivative, and more preferably contains at least one selected from the group consisting of acid-modified hydrogenated rosins and acid-modified rosins.

The acid-modified hydrogenated rosin preferably contains an acrylated hydrogenated rosin.

The acid-modified rosin preferably contains a maleated rosin.

In the flux, the amount of the rosin relative to the total mass (100% by mass) of the flux is preferably 5% by mass to 50% by mass, more preferably 10% by mass to 45% by mass, and even more preferably 15% by mass to 40% by mass.

<<Thixotropic Agent>>

Examples of a thixotropic agent include ester-based thixotropic agents, amide-based thixotropic agents, and sorbitol-based thixotropic agents.

Examples of the ester-based thixotropic agents include ester compounds and specific examples thereof include hardened castor oil and ethyl myristate.

Examples of the amide-based thixotropic agents include monoamides, bisamides, and polyamides.

Examples of the monoamides include lauric acid amide, palmitic acid amide, stearic acid amide, behenic acid amide, hydroxystearic acid amide, saturated fatty acid amide, oleic acid amide, erucic acid amide, unsaturated fatty acid amide, 4-methylbenzamide(p-toluamide), p-toluenemethanamide, aromatic amide, hexamethylene hydroxystearic acid amide, substituted amide, methylolstearic acid amide, methylolamide, and fatty acid ester amide.

Examples of the bisamide include ethylene bis(fatty acid (the carbon number of the fatty acid being 6 to 24)) amide, ethylene bis(hydroxyl fatty acid (the carbon number of the fatty acid being 6 to 24) amide, hexamethylene bis(fatty acid (the carbon number of the fatty acid being 6 to 24)) amide, hexamethylene bis(hydroxyl fatty acid (the carbon number of the fatty acid being 6 to 24)) amide, and aromatic bisamide. Examples of the fatty acid that is a raw material of the bisamide include stearic acid (having 18 carbon atoms), oleic acid (having 18 carbon atoms), and lauric acid (having 12 carbon atoms).

Examples of the polyamide include saturated fatty acid polyamides, unsaturated fatty acid polyamides, aromatic polyamides, 1,2,3-propane tricarboxylic acid tris(2-methylcyclohexylamide), cyclic amide oligomers, and acyclic amide oligomers.

Examples of the cyclic amide oligomers include: amide oligomers in which a dicarboxylic acid and a diamine are cyclically polycondensed; amide oligomers in which a tricarboxylic acid and a diamine are cyclically polycondensed; amide oligomers in which a dicarboxylic acid and a triamine are cyclically polycondensed; amide oligomers in which a tricarboxylic acid and a triamine are cyclically polycondensed; amide oligomers in which a dicarboxylic acid, a tricarboxylic acid and a diamine are cyclically polycondensed; amide oligomers in which a dicarboxylic acid, a tricarboxylic acid and a triamine are cyclically polycondensed; amide oligomers in which a dicarboxylic acid, a diamine and a triamine are cyclically polycondensed; amide oligomers in which a tricarboxylic acid, a diamine and a triamine are cyclically polycondensed; and amide oligomers in which a dicarboxylic acid, a tricarboxylic acid, a diamine and a triamine are cyclically polycondensed.

Examples of the acyclic amide oligomers include: amide oligomers in which a monocarboxylic acid and a diamine and/or triamine are acyclically polycondensed; and amide oligomers in which a dicarboxylic acid and/or tricarboxylic acid and a monoamine are acyclically polycondensed. In the case of an amide oligomer including a monocarboxylic acid or a monoamine, the monocarboxylic acid or the monoamine serves as a terminal molecule to form an acyclic amide oligomer having a small molecular weight.

In the case in which an acyclic amide oligomer is an amide compound in which a dicarboxylic acid and/or tricarboxylic acid, and, a diamine and/or triamine are acyclically polycondensed, the acyclic amide oligomer becomes an acyclic high-molecular-based amide polymer. Additional examples of the acyclic amide oligomers include amide oligomers in which a monocarboxylic acid and a monoamine are acyclically condensed.

Examples of the sorbitol-based thixotropic agent include dibenzylidene-D-sorbitol, bis(4-methylbenzylidene)-D-sorbitol, (D-)sorbitol, monobenzylidene(-D-)sorbitol, and mono(4-methylbenzylidene)-(D-)sorbitol.

One of the thixotropic agents may be used alone or at least two thereof may be mixed and used.

The thixotropic agent preferably contains at least one selected from the group consisting of ester-based thixotropic agents and amide-based thixotropic agents.

The ester-based thixotropic agent preferably contains a hardened castor oil.

The amide-based thixotropic agent preferably contains at least one selected from the group consisting of bisamides and polyamides. The bisamide preferably contains hexamethylene bishydroxy fatty acid amide, and more preferably contains hexamethylene bishydroxy stearic acid amide.

In the flux, the amount of the thixotropic agent relative to the total mass (100% by mass) of the flux is preferably 3% by mass to 20% by mass, more preferably 5% by mass to 15% by mass, and even more preferably 7% by mass to 10% by mass.

<<Solvent>>

Examples of the solvent include water, alcohol-based solvents, glycol ether-based solvent, and terpineols.

Examples of the alcohol-based solvents include isopropyl alcohol, 1,2-butanediol, isobornylcyclohexanol, 2,4-diethyl-1,5-pentanediol, 2,2-dimethyl-1,3-propanediol, 2,5-dimethyl-2,5-hexanediol, 2,5-dimethyl-3-hexine-2,5-diol, 2,3-dimethyl-2,3-butanediol, 2-methylpentane-2,4-diol, 1,1,1-tris(hydroxymethyl)propane, 2-ethyl-2-hydroxymethyl-1,3-propanediol, 2,2'-oxybis(methylene)bis(2-ethyl-1,3-propanediol), 2,2-bis(hydroxymethyl)-1,3-propanediol, 1,2,6-trihydroxyhexane, 1-ethynyl-1-cyclohexanol, 1,4-cyclohexanediol, 1,4-cyclohexanedimethanol, and 2,4,7,9-tetramethyl-5-decyne-4,7-diol.

Examples of the glycol ether-based solvent include diethylene glycol mono-2-ethylhexylether, ethylene glycol monophenyl ether, diethylene glycol monohexyl ether (hexyl diglycol), diethylene glycol dibutyl ether, triethylene glycol monobutyl ether, methylpropylene triglycol, triethylene glycol butyl methylether, tetraethylene glycol dimethylether, and tripropylene glycol-n-butyl ether.

One of the solvents may be used alone or at least two thereof may be mixed and used.

The solvent preferably contains a glycol ether-based solvent, and more preferably contains tripropylene glycol-n-butyl ether.

In the flux, the total amount of the solvent relative to the total mass (100% by mass) of the flux is preferably 30% by mass to 80% by mass, more preferably 35% by mass to 75% by mass, and even more preferably 35% by mass to 60% by mass.

<<Other Activator>>

Examples of an activator other than the organic acids include amines and halogen compounds.

[Amine]

Examples of the amines include rosin amines, azoles, guanidines, alkylamine compounds, and aminoalcohol compounds. Examples of the rosin amines include the same compounds mentioned as the <rosin>.

Examples of the azoles include 2-methylimidazole, 2-ethylimidazole, 2-undecylimidazole, 2-heptadecylimidazole, 1,2-dimethylimidazole, 2-ethyl-4-methylimidazole, 2-phenylimidazole, 2-phenyl-4-methylimidazole, 1-benzyl-2-methylimidazole, 1-benzyl-2-phenylimidazole, 1-cyanoethyl-2-methylimidazole, 1-cyanoethyl-2-undecylimidazole, 1-cyanoethyl-2-ethyl-4-methylimidazole, 1-cyanoethyl-2-phenylimidazole, 1-cyanoethyl-2-undecylimidazolium trimellitate, 1-cyanoethyl-2-phenylimidazolium trimellitate, 2,4-diamino-6-[2'-methylimidazolyl-(1')]-ethyl-s-triazine, 2,4-diamino-6-[2'-undecylimidazolyl-(1')]-ethyl-s-triazine, 2,4-diamino-6-[2'-ethyl-4'-methylimidazolyl-(1')]-ethyl-s-triazine, 2,4-diamino-6-[2'-methylimidazolyl-(1')]-ethyl-s-triazine isocyanuric acid adducts, 2-phenylimidazole isocyanuric acid adducts, 2-phenyl-4,5-dihydroxymethylimidazole, 2-phenyl-4-methyl-5-hydroxymethylimidazole, 2,3-dihydro-1H-pyrrolo[1,2-a]benzimidazole, 1-dodecyl-2-methyl-3-benzylimidazolium chloride, 2-methylimidazoline, 2-phenylimidazoline, 2,4-diamino-6-vinyl-s-triazine, 2,4-diamino-6-vinyl-s-triazine isocyanuric acid adducts, 2,4-diamino-6-methacryloyloxyethyl-s-triazine, epoxy-imidazole adducts, 2-methylbenzimidazole, 2-octylbenzimidazole, 2-pentylbenzimidazole, 2-(1-ethylpentyl)benzimidazole, 2-nonylbenzimidazole, 2-(4-thiazolyl)benzimidazole, benzimidazole, 1,2,4-triazole, 2-(2'-hydroxy-5'-methylphenyl)benzotriazole, 2-(2'-hydroxy-3'-tert-butyl-5'-methylphenyl)-5-chlorobenzotriazole, 2-(2'-hydroxy-3',5'-di-tert-amylphenyl)benzotriazole, 2-(2'-hydroxy-5'-tert-octylphenyl)benzotriazole, 2,2'-methylenebis[6-(2H-benzotriazol-2-yl)-4-tert-octylphenol], 6-(2-benzotriazolyl)-4-tert-octyl-6'-tert-butyl-4'-methyl-2,2'-methylenebisphenol, 1,2,3-benzotriazole, 1-[N,N-bis(2-ethylhexyl)aminomethyl]benzotriazole, carboxybenzotriazole, 1-[N,N-bis(2-ethylhexyl)aminomethyl]methylbenzotriazole, 2,2'-[[(methyl-1H-benzotriazol-1-yl)methyl]imino]bisethanol, 1-(1',2'-dicarboxyethyl)benzotriazole, 1-(2,3-dicarboxypropyl)benzotriazole, 1-[(2-ethylhexylamino)methyl]benzotriazole, 2,6-bis[(1H-benzotriazol-1-yl)methyl]-4-methylphenol, 5-methylbenzotriazole, and 5-phenyltetrazole.

Examples of the guanidines include 1,3-diphenylguanidine, 1,3-di-o-tolylguanidine, 1-o-tolylbiguanide, 1,3-di-o-cumenylguanidine, and 1,3-di-o-cumenyl-2-propionylguanidine.

Examples of the alkylamine compounds include ethylamine, triethylamine, ethylenediamine, triethylenetetramine, cyclohexylamine, hexadecylamine, and stearylamine.

Examples of the aminoalcohol compounds include N,N,N',N'-tetrakis(2-hydroxypropyl)ethylenediamine.

One of the amines may be used alone or at least two thereof may be mixed and used.

The amine preferably contains an azole. The azole preferably contains 2-phenylimidazole.

In the flux, the amount of the amine-based activator relative to the total mass (100% by mass) of the flux is preferably 1% by mass to 10% by mass, and more preferably 2% by mass to 5% by mass.

[Halogen compound]

Examples of the halogen compound include amine hydrohalic acid salts, and organic halogen compounds other than the amine hydrohalic acid salts.

The amine hydrohalic acid salt is a compound obtained by reacting an amine and hydrogen halide.

Examples of the amine include aliphatic amines, azoles, and guanidines.

Examples of the hydrogen halide include hydrogenated products such as such as chlorinated, fluorinated, brominated or iodinated products.

Examples of the aliphatic amines include ethylamine, diethylamine, triethylamine, and ethylene diamine.

Examples of the guanidines and azoles include the same compounds mentioned in the [amine].

More specific examples of the amine hydrohalic acid salts include cyclohexylamine hydrobromide, hexadecylamine hydrobromide, stearylamine hydrobromide, ethylamine hydrobromide, diphenylguanidine hydrobromide, ethylamine hydrochloride, stearylamine hydrochloride, diethylaniline hydrochloride, diethanolamine hydrochloride, 2-ethylhexylamine hydrobromide, pyridine hydrobromide, isopropylamine hydrobromide, diethylamine hydrobromide, dimethylamine hydrobromide, dimethylamine hydrochloride, rosin amine hydrobromide, 2-ethylhexylamine hydrochloride, isopropylamine hydrochloride, cyclohexylamine hydrochloride, 2-pipecoline hydrobromide, 1,3-diphenylguanidine hydrochloride, dimethylbenzylamine hydrochloride, hydrazine hydrate hydrobromide, dimethylcyclohexylamine hydrochloride, trinonylamine hydrobromide, diethylaniline hydrobromide, 2-diethylaminoethanol hydrobromide, 2-diethylaminoethanol hydrochloride, ammonium chloride, diallylamine hydrochloride, diallylamine hydrobromide, diethylamine hydrochloride, triethylamine hydrobromide, triethylamine hydrochloride, hydrazine monohydrochloride, hydrazine dihydrochloride, hydrazine monohydrobromide, hydrazine dihydrobromide, pyridine hydrochloride, aniline hydrobromide, butylamine hydrochloride, hexylamine hydrochloride, n-octylamine hydrochloride, dodecylamine hydrochloride, dimethylcyclohexylamine hydrobromide, ethylenediamine dihydrobromide, rosin amine hydrobromide, 2-phenylimidazole hydrobromide, 4-benzylpyridine hydrobromide, L-glutamic acid hydrochloride, N-methylmorpholine hydrochloride, betaine hydrochloride, 2-pipecoline hydroiodide, cyclohexylamine hydroiodide, 1,3-diphenylguanidine hydrofluoride, diethylamine hydrofluoride, 2-ethylhexylamine hydrofluoride, cyclohexylamine hydrofluoride, ethylamine hydrofluoride, rosin amine hydrofluoride, cyclohexylamine tetrafluoroborate, and dicyclohexylamine tetrafluoroborate.

Furthermore, as the halogen compound, for example, a salt obtained by reacting an amine with tetrafluoroboric acid (HBF$_4$), and a complex obtained by reacting an amine with boron trifluoride (BF$_3$) can also be used.

Examples of the complex include boron trifluoride piperidine.

Examples of the organic halogen compounds other than the amine hydrohalic acid salts include halogenated aliphatic compounds. A halogenated aliphatic hydrocarbon group is a group formed by partially or entirely substituting hydrogen atoms constituting an aliphatic hydrocarbon group with halogen atoms.

Examples of the halogenated aliphatic compounds include halogenated aliphatic alcohols, and halogenated heterocyclic compounds.

Examples of the halogenated aliphatic alcohols include 1-bromo-2-propanol, 3-bromo-1-propanol, 3-bromo-1,2-propanediol, 1-bromo-2-butanol, 1,3-dibromo-2-propanol, 2,3-dibromo-1-propanol, 1,4-dibromo-2-butanol, and trans-2,3-dibromo-2-butene-1,4-diol.

Examples of the halogenated heterocyclic compounds include compounds of the following general formula (1).

[In the formula, $R^{71}$ is an n-valent heterocyclic group. $R^{72}$ is a halogenated aliphatic hydrocarbon group.]

Examples of a hetero ring of the n-valent heterocyclic group as $R^{71}$ include a ring structure formed by partially substituting carbon atoms constituting an aliphatic hydrocarbon ring or an aromatic hydrocarbon ring with hetero atoms. Examples of the hetero atom in the hetero ring include an oxygen atom, a sulfur atom and a nitrogen atom.

The hetero ring is preferably a three- to ten-membered ring, and more preferably a five- to seven-membered ring. Examples of the hetero ring include an isocyanurate ring.

The carbon number of the halogenated aliphatic hydrocarbon group as $R^{72}$ is preferably one to ten, more preferably two to six, and even more preferably three to five. $R^{72}$ is preferably a brominated aliphatic hydrocarbon group or a chlorinated aliphatic hydrocarbon group, more preferably a brominated aliphatic hydrocarbon group, and even more preferably a brominated saturated aliphatic hydrocarbon group.

Examples of the halogenated heterocyclic compound include tris(2,3-dibromopropyl)isocyanurate.

Examples of the organic halogen compound other than the amine hydrohalic acid salts include halogenated carboxyl compounds such as iodized carboxyl compounds such as 2-iodobenzoic acid, 3-iodobenzoic acid, 2-iodopropionic acid, 5-iodosalicylic acid, and 5-iodoanthranilic acid; chlorinated carboxyl compounds such as 2-chlorobenzoic acid, and 3-chloropropionic acid; and brominated carboxyl compounds such as 2,3-dibromopropionic acid, 2,3-dibromosuccinic acid, and 2-bromobenzoic acid.

One of the halogen-based activators may be used alone or at least two thereof may be mixed and used.

The halogen-based activator preferably contains an organic halogen compound other than amine hydrohalic acid salts, and more preferably contains 2,3-dibromosuccinic acid.

In the flux, the amount of the halogen-based activator relative to the total mass (100% by mass) of the flux is preferably 0.01% by mass to 2% by mass, and more preferably 0.01% by mass to 1% by mass.

Resin components other than rosin-based resins:

Examples of the resin component other than the rosin-based resins include terpene resin, modified terpene resin, terpene phenol resin, modified terpene phenol resin, styrene resin, modified styrene resin, xylene resin, modified xylene resin, acrylic resin, polyethylene resin, acryl-polyethylene copolymer resin, and epoxy resin.

Examples of the modified terpene resin include aromatic modified terpene resin, hydrogenated terpene resin, and hydrogenated aromatic modified terpene resin.

Examples of the modified terpene phenol resin include hydrogenated terpene phenol resin.

Examples of the modified styrene resin include styrene acrylic resin, and styrene maleic resin. Examples of the modified xylene resin include phenol-modified xylene resin, alkylphenol-modified xylene resin, phenol-modified resol-type xylene resin, polyol modified xylene resin, and polyoxyethylene-added xylene resin.

<<Metal Deactivator>>

Examples of the metal deactivator include hindered phenol-based compounds, and nitrogen compounds.

The term "metal deactivator" refers to a compound that can prevent metal from deteriorating when in contact with a certain compound.

The hindered phenol-based compound is a phenol-based compound having a bulky substituent (such as a branched alkyl group such as a t-butyl group or a cyclic alkyl group) on at least one of ortho positions of a phenol.

Although the hindered phenol-based compound is not particularly limited, examples thereof include bis[3-(3-tert-butyl-4-hydroxy-5-methylphenyl)propionic acid][ethylenebis(oxyethylene)], N,N'-hexamethylenebis[3-(3,5-di-tert-butyl-4-hydroxyphenyl)propaneamide], 1,6-hexanediolbis[3-(3,5-di-tert-butyl-4-hydroxyphenyl)propionate], 2,2'-methylenebis[6-(1-methylcyclohexyl)-p-cresol], 2,2'-methylenebis(6-tert-butyl-p-cresol), 2,2'-methylenebis(6-tert-butyl-4-ethylphenol), triethylene glycol-bis[3-(3-tert-butyl-5-methyl-4-hydroxyphenyl)propionate], 1,6-hexanediol-bis-[3-(3,5-di-tert-butyl-4-hydroxyphenyl)propionate], 2,4-bis-(n-octylthio)-6-(4-hydroxy-3,5-di-t-butylanilino)-1,3,5-triazine, pentaerythrityl-tetrakis[3-(3,5-di-tert-butyl-4-hydroxyphenyl)propionate], 2,2-thiodiethylenebis[3-(3,5-di-tert-butyl-4-hydroxyphenyl)propionate], octadecyl-3-(3,5-di-tert-butyl-4-hydroxyphenyl)propionate, N,N'-hexamethylenebis(3,5-di-t-butyl-4-hydroxy-hydrocinnamamide), 3,5-di-tert-butyl-4-hydroxybenzylphosphonate-diethyl esters, 1,3,5-trimethyl-2,4,6-tris(3,5-di-tert-butyl-4-hydroxybenzyl)benzene, N,N'-bis[2-[2-(3,5-di-tert-butyl-4-hydroxyphenyl)ethylcarbonyloxy]ethyl]oxamide, and compounds of the following formula.

[Chemical formula 16]

(In the formula, Z is an alkylene group which may have a substituent. $R^{81}$ and $R^{82}$ are each independently an alkyl group, an aralkyl group, an aryl group, a heteroaryl group, a cycloalkyl group or a heterocycloalkyl group, which may have a substituent. $R^{83}$ and $R^{84}$ are each independently an alkyl group which may have a substituent.)

Examples of the nitrogen compound as the metal deactivator include hydrazide-based nitrogen compounds, amide-based nitrogen compounds, triazole-based nitrogen compounds and melamine-based nitrogen compounds.

The hydrazide-based nitrogen compound may be a nitrogen compound having a hydrazide skeleton, and examples thereof include dodecanedioic acid bis[N2-(2hydroxybenzoyl)hydrazide], N,N'-bis[3-(3,5-di-tert-butyl-4-hydroxyphenyl)propionyl]hydrazine, decanedicarboxylic acid disalicyloylhydrazide, N-salicylidene-N'-salicylhydrazide, m-nitrobenzhydrazide, 3-aminophthalhydrazide, phthalic acid dihydrazide, adipic acid hydrazide, oxalobis(2-hydroxy-5-octylbenzylidenehydrazide), N'-benzoylpyrrolidone carboxylic acid hydrazide, and N,N'-bis(3-(3,5-di-tert-butyl-4-hydroxyphenyl)propionyl)hydrazine.

The amide-based nitrogen compound may be a nitrogen compound having an amide skeleton, and examples thereof include N,N'-bis{2-[3-(3,5-di-tert-butyl-4-hydroxyphenyl)propionyloxy]ethyl}oxamide.

The triazole-based nitrogen compound may be a nitrogen compound having a triazole skeleton, and examples thereof include N-(2H-1,2,4-triazol-5-yl)salicylamide, 3-amino-1,2,4-triazole, and 3-(N-salicyloyl)amino-1,2,4-triazole.

The melamine-based nitrogen compound may be a nitrogen compound having a melamine skeleton, and examples thereof include melamine, and melamine derivatives.

Specific examples thereof include trisaminotriazine, alkylated trisaminotriazine, alkoxyalkylated trisaminotriazine, melamine, alkylated melamine, alkoxyalkylated melamine, N2-butylmelamine, N2,N2-diethylmelamine, and N,N,N',N',N'',N''-hexakis(methoxymethyl)melamine.

One of the metal deactivators may be used alone or at least two thereof may be mixed and used.

The metal deactivator preferably contains at least one selected from the group consisting of hindered phenol-based compounds and triazole-based nitrogen compounds.

The triazole-based nitrogen compound preferably contains N-(2H-1,2,4-triazol-5-yl)salicylamide.

In the flux, the amount of the metal deactivator relative to the total mass (100% by mass) of the flux is preferably 1% by mass to 10% by mass, and more preferably 2% by mass to 5% by mass.

<<Surfactant>>

Examples of the surfactant include nonionic surfactants and weak cationic surfactants.

Examples of the nonionic surfactants include polyethylene glycol, polyethylene glycol-polypropylene glycol copolymers, aliphatic alcohol polyoxyethylene adducts, aromatic alcohol polyoxyethylene adducts, and polyhydric alcohol polyoxyethylene adducts.

Examples of the weak cationic surfactants include diamine-terminated polyethylene glycol, diamine-terminated polyethylene glycol-polypropylene glycol copolymers, aliphatic amine polyoxyethylene adducts, aromatic amine polyoxyethylene adducts, and polyvalent amine polyoxyethylene adducts.

Examples of surfactants other than the above-mentioned surfactants include polyoxyalkylene acetylene glycols, polyoxyalkylene glyceryl ethers, polyoxyalkylene alkyl ethers, polyoxyalkylene esters, polyoxyalkylene alkylamines, and polyoxyalkylene alkylamides.

The flux according to the above-mentioned embodiment makes it possible to suppress a viscosity increase of a solder paste over time and to enhance aggregability of a solder at the time of reflow by containing both a chelate agent containing a compound having a five-membered ring structure consisting of nitrogen atoms, sulfur atoms and carbon atoms and an organic sulfonic acid.

Although the reason such effects are exhibited is not clear, the following is assumed. The compound (C) contained in the flux according to the present embodiment serves as a chelate agent to protect the metal surface of the solder powder. Thus, a reaction between an activator contained in the flux and the solder powder is suppressed, thereby suppressing the viscosity increase of a solder paste over time. However, the compound (C) contained in the flux decreases the aggregability of a melted solder, thereby facilitating the formation of solder balls. Although the flux contains the compound (C), the flux contains an organic sulfonic acid, thereby suppressing the formation of solder balls and enhancing the aggregability of the solder at the time of reflow.

(Solder Paste)

A solder paste of the present embodiment contains a solder alloy powder and the above-mentioned flux.

The solder alloy powder may be composed of an Sn-only solder powder; or a powder of an Sn—Ag-based, Sn—Cu-based, Sn—Ag—Cu-based, Sn—Bi-based, or Sn—In-based solder alloy, or a powder of solder alloys in which Sb, Bi, In, Cu, Zn, As, Ag, Cd, Fe, Ni, Co, Au, Ge, P, or the like has been added to the above-mentioned alloys.

The solder alloy powder may be composed of a powder of an Sn—Pb-based solder alloy, or a powder of a solder alloy in which Sb, Bi, In, Cu, Zn, As, Ag, Cd, Fe, Ni, Co, Au, Ge, P, or the like has been added to the Sn—Pb-based solder alloy.

The solder alloy powder is preferably a Pb-free solder.

Amount of flux: In the solder paste, the amount of the flux relative to the total mass of the solder paste is preferably 5% by mass to 30% by mass, and more preferably 5% by mass to 15% by mass.

Since the solder paste of the present embodiment contains the flux containing a compound (C) having a five-membered ring structure consisting of nitrogen atoms, sulfur atoms and carbon atoms and an organic sulfonic acid, the viscosity increase of the solder paste over time can be suppressed and the aggregability of the solder at the time of reflow can be enhanced.

EXAMPLES

Hereinafter, the present invention will be described with reference to examples, but the present invention is not limited to the following examples.

<Preparation of Flux>

Examples 1 to 12 and Comparative Examples 1 to 4

Each flux of examples and comparative examples was prepared using the constitution shown in Tables 1 and 2. Raw materials used are shown below.

Compound (C): 2-mercaptobenzothiazole, 2,5-dimercapto-1,3,4-thiadiazole, 2-(methylthio)-2-thiazoline Other chelate agent: 2-mercaptopyridine Organic sulfonic acid: methanesulfonic acid, p-toluenesulfonic acid Other organic acid: glutaric acid, azelaic acid, adipic acid Halogen compound: 2,3-dibromosuccinic acid Amine: 2-phenylimidazole Rosin: acrylated hydrogenated rosin, maleated rosin Thixotropic agent: polyamide, hardened castor oil, hexamethylene bishydroxystearic acid amide Metal deactivator: N-(2H-1,2,4-triazol-5-yl)salicylamide, hindered phenol-based antioxidant Solvent: tripropylene glycol-n-butyl ether <Preparation of Solder Paste>

A solder-paste was prepared by mixing the flux of each example with the following solder alloy powder (1) or solder alloy powder (2). Each of the prepared solder pastes contained 10.5% by mass of the flux and 89.5% by mass of the solder alloy powder.

As the solder alloy powder, the solder alloy powder (1), or the solder alloy powder (2) was used. Each of the solder alloy powder (1) and the solder alloy powder (2) had a size (particle size distribution) satisfying symbol 4 in the powder size classification (Table 2) in JIS Z 3284-1:2014.

The solder alloy powder (1) was a solder alloy consisting of 58% by mass of Bi, 2% by mass of In, 0.03% by mass of Pd, and a balance of Sn. The liquid phase line of the solder alloy powder (1) was 139° C. and the solid phase line thereof was 133° C.

The solder alloy powder (2) was a solder alloy consisting of 3% by mass of Ag, 3% by mass of In, 3% by mass of Bi and a balance of Sn.

Each flux of Examples 1 to 11 and Comparative Examples 1 to 4 was mixed with a solder alloy powder (1) to prepare a solder paste. In addition, a flux of Example 12 was mixed with a solder alloy powder (2) to prepare a solder paste.

The thus prepared solder paste was subjected to <<evaluation of viscosity stability over time>>, <<evaluation of aggregability of solder>> and <<evaluation of suppressibility of solder ball formation>> by the evaluation methods described in the following <Evaluation>. The evaluation results are shown in Tables 1 and 2.

<Evaluation>

<<Evaluation of Viscosity Stability Over Time>>

(1) Evaluation Method

The viscosity of the resultant solder paste was continuously measured for 10 hours in accordance with a method described in "4.2 Viscosity characteristic test" of JIS Z 3284-3:2014 using a rotation viscometer (PCU-205, manufactured by MALCOM COMPANY LIMITED) at a rotation speed of 10 rpm at a measurement temperature of 25° C. Then, the initial viscosity (viscosity 30 minutes after the initiation of measurement) and the viscosity ten hours after the initiation of measurement were compared to conduct evaluation of viscosity stability over time in accordance with the following evaluation criteria.

(2) Evaluation Criteria

A: Viscosity ten hours after the initiation of measurement <Initial viscosity×1.1 The viscosity increase over time was small and particularly favorable.

B: Initial viscosity×1.1≤Viscosity ten hours after the initiation of measurement <Initial viscosity×1.3 The viscosity increase over time was confirmed, but favorable.

C: Initial viscosity×1.3≤Viscosity ten hours after the initiation of measurement The viscosity increase over time was large and unfavorable.

<<Evaluation of Aggregability of Solder>>

(1) Evaluation Method

The degree of solder agglomeration of each resultant solder paste was evaluated in accordance with the method described in "4.2 Solder ball test" of JIS Z 3284-4:2014.

Specifically, the solder paste of each example was printed using a squeegee on a ceramic substrate (25 mm×50 mm×0.2 mm) using a metal mask (25 mm×50 mm×0.2 mm, hole size 6.5 mm). Then, the metal mask was peeled off to obtain a sample of each example.

Then, the solder surface of a solder bath set at a temperature higher than the liquid phase line temperature by 35±3° C. was cleaned with a scrubber. Next, the sample was horizontally placed on the solder liquid surface within one hour after the solder paste was printed on the substrate, and the sample was horizontally removed from the solder liquid surface five seconds after the solder paste melted, followed by leaving the sample to cool until the solder of the sample was solidified.

Evaluation was performed in accordance with the following criteria.
(2) Evaluation Criteria
1: The solder (powder) melted into a single large ball with no solder balls therearound.
2: The solder (powder) melted into a single large ball with three or less solder balls having a diameter of 75 m or less therearound.
3: The solder (powder) melted into a single large ball with four or more solder balls having a diameter of 75 μm or less therearound, the solder balls not being arranged in a semi-continuous ring.
4: The solder (powder) melted into a single large ball with a large number of fine balls arranged in a semi-continuous ring therearound.
5: Other than the above <<Evaluation of Suppressibility of Solder Ball Formation>>
(1) Evaluation Method
A metal mask (mask thickness 0.12 mm) was used to print a solder paste on a substrate having 128 dot-like electrodes (<p 0.4 mm), and then reflow was performed. Reflow was performed with profile (1) or profile (2).

Figure 1:
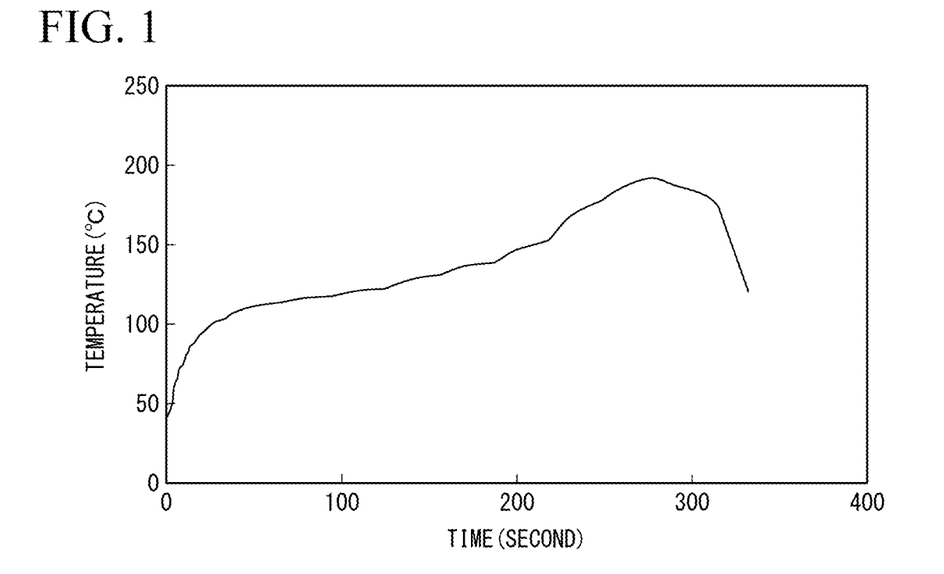
FIG. 1 is a drawing showing a reflow profile (1) in an evaluation of suppressibility of solder ball formation.

In profile (1), the temperature was raised from 50° C. to 100° C. for 23 seconds, held at 100° C. to 120° C. for 78 seconds, and then held at 150° C. or higher for 114 seconds, with a peak at 192.3° C. The reflow atmosphere was a nitrogen atmosphere with an oxygen concentration of 1000 ppm. A graph showing profile (1) is shown in FIG. 1.

Figure 2:
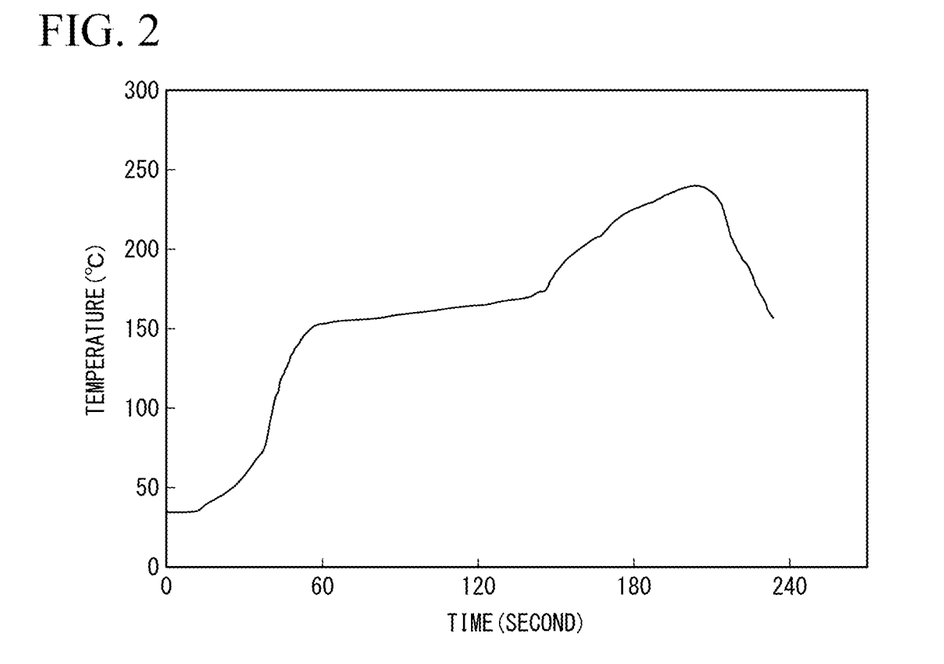
FIG. 2 is a drawing showing a reflow profile (2) in an evaluation of suppressibility of solder ball formation.

In Profile (2), preheating was conducted by holding the temperature at 150° C. to 175° C. for 90 seconds and then at 220° C. or higher for 41 seconds, with a peak at 240° C.

The reflow atmosphere was a nitrogen atmosphere with an oxygen concentration of 1000 ppm. A graph showing profile (2) is shown in FIG. 2.

After reflow, the number of solder balls on the 128 electrodes was counted.
(2) Evaluation Criteria
A: The number of formed solder balls was 20 or less, and the suppressibility of solder ball formation was particularly favorable.
B: The number of formed solder balls was more than 20 and less than 100, and the suppressibility of solder ball formation was favorable.
C: The number of formed solder balls was 100 or more, or solder remained without being melted, and the suppressibility of solder ball formation was unfavorable.

TABLE 1

|  |  |  | Ex. 1 | Ex. 2 | Ex. 3 | Ex. 4 | Ex. 5 | Ex. 6 | Ex. 7 | Ex. 8 |
|---|---|---|---|---|---|---|---|---|---|---|
| Chelate agent | Compound (C) | 2-Mercaptobenzothiazole | 0.3 | 0.5 | 1 | 1 | 1 | 3 | 3 | 3 |
|  |  | 2,5-Dimercapto-1,3,4-thiadiazole |  |  |  |  |  |  |  |  |
|  |  | 2-(Methylthio)-2-thiazoline |  |  |  |  |  |  |  |  |
|  | Other chelate agent | 2-Mercaptopyridine |  |  |  |  |  |  |  |  |
| Organic acid | Organic sulfonic acid | Methanesulfonic acid | 1 | 1 | 0.5 | 1 | 1.5 | 0.5 | 1 | 1.5 |
|  |  | p-Toluenesulfonic acid |  |  |  |  |  |  |  |  |
|  | Other organic acid | Glutaric acid | 3 | 3 | 3 | 3 | 3 | 3 | 3 | 3 |
|  |  | Azelaic acid | 5 | 5 | 5 | 5 | 5 | 5 | 5 | 5 |
|  |  | Adipic acid | 2 | 2 | 2 | 2 | 2 | 2 | 2 | 2 |
| Halogen compound |  | 2,3-Dibromosuccinic acid | 0.04 | 0.04 | 0.04 | 0.04 | 0.04 | 0.04 | 0.04 | 0.04 |
| Amine |  | 2-Phenylimidazole | 3 | 3 | 3 | 3 | 3 | 3 | 3 | 3 |
| Rosin |  | Acrylated hydrogenated rosin | 21.6 | 21.6 | 21.6 | 21.6 | 21.6 | 21.6 | 21.6 | 21.6 |
|  |  | Maleated rosin | 9 | 9 | 9 | 9 | 9 | 9 | 9 | 9 |
| Thixotropic agent |  | Polyamide | 1.5 | 1.5 | 1.5 | 1.5 | 1.5 | 1.5 | 1.5 | 1.5 |
|  |  | Hardened castor oil | 1.3 | 1.3 | 1.3 | 1.3 | 1.3 | 1.3 | 1.3 | 1.3 |
|  |  | Hexamethylene bishydroxystearic acid amide | 5 | 5 | 5 | 5 | 5 | 5 | 5 | 5 |
| Metal deactivator |  | N-(2H-1,2,4-triazol-5-yl) salicylamide |  | 0.2 | 0.2 | 0.2 | 0.2 | 0.2 | 0.2 | 0.2 |
|  |  | Hindered phenol-based antioxidant | 3.6 | 3.6 | 3.6 | 3.6 | 3.6 | 3.6 | 3.6 | 3.6 |
| Solvent |  | Tripropylene glycol-n-butyl ether | 43.66 | 43.26 | 43.26 | 42.76 | 42.26 | 41.26 | 40.76 | 40.26 |
| Total (% by mass) |  |  | 100 | 100 | 100 | 100 | 100 | 100 | 100 | 100 |
| Organic sulfonic acid/Particular chelate agent |  |  | 3.33 | 2.00 | 0.50 | 1.00 | 1.50 | 0.17 | 0.33 | 0.50 |

TABLE 1-continued

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| Organic sulfonic acid/Organic acid | 0.091 | 0.091 | 0.048 | 0.091 | 0.130 | 0.048 | 0.091 | 0.130 |
| Evaluation of viscosity stability over time | B | A | A | A | A | A | A | A |
| Evaluation of solder aggregability | 3 | 3 | 3 | 3 | 3 | 3 | 3 | 3 |
| Suppressibility of solder ball formation | A | A | B | A | A | B | A | A |

(Ex.: Example)

TABLE 2

| | | | Ex. 9 | Ex. 10 | Ex. 11 | Ex. 12 | C.Ex. 1 | C.Ex. 2 | C.Ex. 3 | C.Ex. 4 |
|---|---|---|---|---|---|---|---|---|---|---|
| Chelate agent | Compound (C) | 2-Mercaptobenzothiazole | 1 | | | 0.5 | 1 | | | |
| | | 2,5-Dimercapto-1,3,4-thiadiazole | | 0.1 | | | | | | |
| | | 2-(Methylthio)-2-thiazoline | | | 0.1 | | | | | |
| | Other chelate agent | 2-Mercaptopyridine | | | | | | | | 0.5 |
| Organic acid | Organic sulfonic acid | Methanesulfonic acid | | 1 | 1 | 1 | | | 1 | 1 |
| | | p-Toluenesulfonic acid | 0.5 | | | | | | | |
| | Other organic acid | Glutaric acid | 3 | 3 | 3 | 3 | 3 | 3 | 3 | 3 |
| | | Azelaic acid | 5 | 5 | 5 | 5 | 5 | 5 | 5 | 5 |
| | | Adipic acid | 2 | 2 | 2 | 2 | 2 | 2 | 2 | 2 |
| Halogen compound | | 2,3-Dibromosuccinic acid | 0.04 | 0.04 | 0.04 | 0.04 | 0.04 | 0.04 | 0.04 | 0.04 |
| Amine | | 2-Phenylimidazole | 3 | 3 | 3 | 3 | 3 | 3 | 3 | 3 |
| Rosin | | Acrylated hydrogenated rosin | 21.6 | 21.6 | 21.6 | 21.6 | 21.6 | 21.6 | 21.6 | 21.6 |
| | | Maleated rosin | 9 | 9 | 9 | 9 | 9 | 9 | 9 | 9 |
| Thixotropic agent | | Polyamide | 1.5 | 1.5 | 1.5 | 1.5 | 1.5 | 1.5 | 1.5 | 1.5 |
| | | Hardened castor oil | 1.3 | 1.3 | 1.3 | 1.3 | 1.3 | 1.3 | 1.3 | 1.3 |
| | | Hexamethylene bishydroxystearic acid amide | 5 | 5 | 5 | 5 | 5 | 5 | 5 | 5 |
| Metal deactivator | | N-(2H-1,2,4-triazol-5-yl)salicylamide | 0.2 | 0.2 | 0.2 | 0.2 | 0.2 | 0.2 | 0.2 | 0.2 |
| | | Hindered phenol-based antioxidant | 3.6 | 3.6 | 3.6 | 3.6 | 3.6 | 3.6 | 3.6 | 3.6 |
| Solvent | | Tripropylene glycol-n-butyl ether | 43.26 | 43.66 | 43.66 | 43.26 | 43.76 | 44.76 | 43.76 | 43.26 |
| Total (% by mass) | | | 100 | 100 | 100 | 100 | 100 | 100 | 100 | 100 |
| Organic sulfonic acid/Particular chelate agent | | | 0.50 | 10.00 | 10.00 | 2.00 | 0.00 | — | — | — |
| Organic sulfonic acid/Organic acid | | | 0.048 | 0.091 | 0.091 | 0.091 | 0.000 | 0.000 | 0.91 | 0.091 |
| Evaluation of viscosity stability over time | | | A | A | A | A | A | C | C | C |
| Evaluation of solder aggregability | | | 3 | 3 | 3 | 3 | 4 | 4 | 3 | 3 |
| Suppressibility of solder ball formation | | | B | A | A | A | C | C | A | A |

(Ex.: Example, C.Ex.: Comparative Example)

The fluxes of Examples 1 to 12 each containing a particular chelate agent (compound (C)) and an organic sulfonic acid could suppress the viscosity increase of the solder paste over time and could enhance the solder agglomeration at the time of reflow.

In contrast, the flux of Comparative Example 2 free from both a particular chelate agent and an organic sulfonic acid could not suppress the viscosity increase of a solder paste over time, and could not sufficiently enhance the solder agglomeration at the time of reflow.

The flux of Comparative Example 1 free from an organic sulfonic acid could not sufficiently enhance the solder agglomeration at the time of reflow.

The fluxes of Comparative Examples 3 and 4 free from a particular chelate agent could not suppress the viscosity increase of the solder paste over time.

It was confirmed from the comparison among Examples 3 to 5 and Examples 6 to 8 that in the case where a flux in which the amount of the organic sulfonic acid relative to the total mass (100% by mass) of the organic acid was 5% by mass or more was used, the suppressibility of solder ball formation was further enhanced.

INDUSTRIAL APPLICABILITY

According to the present invention, a flux and a solder paste which can suppress the viscosity increase of a solder paste over time and enhance the aggregability of a solder at the time of reflow can be provided. The long-term storage stability of the flux and the solder paste is excellent. In addition, the flux and the solder paste can be favorably used to solder a substrate subjected to a surface-treatment.

The invention claimed is:

1. A flux comprising: a chelate agent; and an organic acid, wherein
the chelate agent comprises at least one compound (C) selected from the group consisting of a compound (C1) of general formula (1), a compound (C3) of general formula (3), and a compound (C7) of general formula (7), and
the organic acid comprises at least one organic sulfonic acid selected from the group consisting of methanesulfonic acid and p-toluenesulfonic acid, in the general formula (1), $R^{11}$ is selected from the group consisting of an organic group, $-SR^{101}$, a hydrogen atom and a halogen atom wherein $R^{101}$ is an organic group or a hydrogen atom, $R^{12}$ is a substituent; and n1 is an integer of 0 to 4;
in the general formula (3), $R^{31a}$ and $R^{31b}$ are each independently selected from the group consisting of an organic group, $-SR^{301}$, a hydrogen atom and a halogen atom wherein $R^{301}$ is an organic group or a hydrogen atom, and
in the general formula (7), $R^{41}$ is selected from the group consisting of an organic group, $-SR^{401}$, a hydrogen atom and a halogen atom wherein $R^{401}$ is an organic group or a hydrogen atom, $R^{42a}$ and $R^{42b}$ are each independently selected from an organic group, $-SR^{402}$, a hydrogen atom and a halogen atom wherein $R^{402}$ is an organic group or a hydrogen atom, and $R^{43a}$ and $R^{43b}$ are each independently selected from an organic group, $-SR^{403}$, a hydrogen atom and a halogen atom wherein $R^{403}$ is an organic group or a hydrogen atom.

2. The flux according to claim 1, wherein an amount of the compound (C) relative to a total mass of the flux is 0.1% by mass to 3% by mass.

3. The flux according to claim 1, wherein a mass ratio of an amount of the organic sulfonic acid relative to a total mass of the compound (C) is 0.3 to 10.

4. The flux according to claim 1, further comprising a rosin.

5. The flux according to claim 1, further comprising a thixotropic agent.

6. A solder paste comprising: a solder alloy powder; and a flux of claim 1.

7. The flux according to claim 1, wherein the organic acid comprises at least one of other organic acids different from the organic sulfonic acid.

8. The flux according to claim 7, wherein an amount of the organic sulfonic acid relative to a total mass of the organic acid is 1% by mass or more.

9. The flux according to claim 8, wherein the amount of the organic sulfonic acid relative to the total mass of the organic acid is 3% by mass to 30% by mass.

10. The flux according to claim 7, wherein a number of formed solder balls is less than 100 in an evaluation of suppressibility of solder ball formation.

11. The flux according to claim 8, wherein a number of formed solder balls is less than 100 in an evaluation of suppressibility of solder ball formation.

12. The flux according to claim 9, wherein a number of formed solder balls is less than 100 in an evaluation of suppressibility of solder ball formation.

* * * * *